United States Patent [19]

Pedain et al.

[11] Patent Number: 5,043,092
[45] Date of Patent: Aug. 27, 1991

[54] PROCESS FOR THE PRODUCTION OF POLYISOCYANATE MIXTURES CONTAINING URETDIONE AND ISOCYANURATE GROUPS

[75] Inventors: Josef Pedain, Cologne; Klaus König, Odenthal; Winfried Dell, Leverkusen, all of Fed. Rep. of Germany

[73] Assignee: Bayer Aktiengesellschaft, Leverkusen, Fed. Rep. of Germany

[21] Appl. No.: 323,538

[22] Filed: Mar. 13, 1989

[30] Foreign Application Priority Data

Mar. 19, 1988 [DE] Fed. Rep. of Germany ....... 3809261

[51] Int. Cl.$^5$ ............................................. C08G 18/72
[52] U.S. Cl. ............................. 252/182.21; 252/182.2; 528/51; 528/67
[58] Field of Search .................... 252/182.1, 182.21; 528/51, 67

[56] References Cited

U.S. PATENT DOCUMENTS

| | | | |
|---|---|---|---|
| 4,284,730 | 8/1981 | Narayan et al. | 252/182.21 |
| 4,442,280 | 4/1984 | Grögler et al. | 252/182.2 |
| 4,639,502 | 1/1987 | Müller et al. | 252/182.2 |
| 4,663,377 | 5/1987 | Hombach et al. | 252/182.2 |
| 4,801,663 | 1/1989 | Ueyanagi et al. | 252/182.21 |
| 4,937,012 | 6/1990 | Kan et al. | 252/182.21 |

FOREIGN PATENT DOCUMENTS 3437635 4/1986 Fed. Rep. of Germany .
1153815 5/1969 United Kingdom .

*Primary Examiner*—John Knight, III
*Assistant Examiner*—Dennis R. Daley
*Attorney, Agent, or Firm*—Joseph C. Gil; Thomas W. Roy

[57] ABSTRACT

The present invention is directed to a process for the production of polyisocyanate mixtures containing isocyanurate groups and uretdione groups in a molar ratio of about 1:9 to 9:1 by oligomerizing a portion of the isocyanate groups of hexamethylene diisocyanate using trialkyl phosphines and/or peralkylated phosphorus acid triamides as the catalysts which accelerate the dimerization and trimerization of isocyanate groups, terminating the reaction at the desired degree of oligomerization by the addition of a catalyst poison and removing unreacted hexamethylene diisocyanate to a residual content of at most 0.5% by weight, characterized in that, before addition of the catalyst, the hexamethylene diisocyanate starting material is freed from carbon dioxide to a residual content of less than 20 ppm (weight).

The present invention is also directed to the polyisocyanates containing uretdione groups and isocyanurate groups obtainable by this process and their use, optionally blocked by blocking agents for isocyanate groups, as the isocyanate component for the production of polyisocyanate polyaddition products.

16 Claims, No Drawings

PROCESS FOR THE PRODUCTION OF POLYISOCYANATE MIXTURES CONTAINING URETDIONE AND ISOCYANURATE GROUPS

BACKGROUND OF THE INVENTION

1. Field of the Invention

This invention relates to a new process for the production of polyisocyanates containing uretdione and isocyanurate groups, i.e. polyisocyanate mixtures, by the oligomerization of a portion of the isocyanate groups of hexamethylene diisocyanate (hereinafter referred to as "HDI") using catalysts which accelerate both dimerization (uretdione formation) and also trimerization (isocyanurate formation), to the products obtained by this process and their use, optionally in blocked form, as the isocyanate component in polyurethane lacquers.

2. Description of the Prior Art

The production of polyisocyanate mixtures containing uretdione and isocyanurate groups by the dimerization and/or trimerization of a portion of the isocyanate groups of organic polyisocyanates using phosphorus-containing catalysts is known. These mixtures are known to be valuable starting materials for the production of polyurethane plastics. However, known processes for the production of such polyisocyanate mixtures using HDI as the starting material (cf. for example DE-OS 1,670,720 and DE-OS 3,432,081) are not optimally suited to large-scale production. The disadvantages of the known processes are the long reaction time and the relatively large quantities of catalyst which result in the need for a correspondingly large quantity of deactivators such that the end product contains a relatively high percentage of unwanted foreign components which adversely affect the properties of the polyurethane plastic.

In the process according to DE-OS 3,437,635, considerable quantities of alcohols are used as co-catalysts which means that valuable isocyanate groups are consumed, i.e. destroyed, by the addition reaction which takes place between isocyanate groups and hydroxyl groups.

Accordingly, an object of the present invention is to provide a new process for the production of HDI-based isocyanate mixtures containing uretdione and isocyanurate groups which is not attended by any of the disadvantages mentioned above.

According to the invention, this object is achieved by using HDI which is substantially free from carbon dioxide as the starting material. It is possible in this way to limit the reaction time to less than one working day, i.e., to less than 10 hours, and at the same time to carry out the process using minimal quantities of catalysts and without using large quantities of co-catalysts which consume isocyanate groups.

SUMMARY OF THE INVENTION

The present invention is directed to a process for the production of polyisocyanate mixtures containing isocyanurate groups and uretdione groups in a molar ratio of about 1:9 to 9:1 by oligomerizing a portion of the isocyanate groups of hexamethylene diisocyanate using trialkyl phosphines and/or peralkylated phosphorus acid triamides as the catalysts which accelerate the dimerization and trimerization of isocyanate groups, terminating the reaction at the desired degree of oligomerization by the addition of a catalyst poison and removing unreacted hexamethylene diisocyanate to a residual content of at most 0.5% by weight, characterized in that, before addition of the catalyst, the hexamethylene diisocyanate starting material is freed from carbon dioxide to a residual content of less than 20 ppm (weight).

The present invention is also directed to the polyisocyanates containing uretdione groups and isocyanurate groups obtainable by this process and their use, optionally blocked by blocking agents for isocyanate groups, as the isocyanate component for the production of polyisocyanate polyaddition products.

DETAILED DESCRIPTION OF THE INVENTION

The use of HDI which is substantially free from carbon dioxide as starting material is critical to the present invention. The HDI used in accordance with the invention contains less than 20 ppm (weight), preferably less than 10 ppm (weight) and more preferably less than 5 ppm (weight) of carbon dioxide.

Technical HDI purified by distillation, of the type previously used for the production of polyisocyanates containing isocyanurate groups, contains considerable quantities (approx. 20 ppm to 100 ppm (weight)) of carbon dioxide. Carbon dioxide can enter the HDI during the production process, for example during the phosgenation of carbonic acid salts of hexamethylene diamine. It can be taken up from the air during storage and can be formed by chemical reaction of the NCO groups to form carbodiimide groups or by reaction with a trace of moisture. After 24 hours in a sealed container HDI, which has been freshly purified by vacuum distillation contains, for example, 40 ppm carbon dioxide. HDI stored over a period of approximately 6 months can contain up to 0.6% by weight of carbon dioxide when the container has been opened during the period of storage.

Carbon dioxide is known to react with uretdione groups to form unwanted secondary products containing oxadiazinone groups. The formation of secondary products with carbon dioxide is mentioned in DE-OS 1,670,720. However, there was no recognition of the considerable influence carbon dioxide has on the catalyst and on the reaction time, nor that standard distillation is unable to adequately reduce the carbon dioxide content in HDI.

Carbon dioxide can be removed from HDI by blowing out with ultrapure nitrogen or with a noble gas, for example argon, for example at about 0° to 120° C., preferably about 0° to 70° C. and more preferably about 30° to 50° C. Although higher temperatures may also be applied, this does not provide any advantages. Carbon dioxide can also be removed by distillation in a stream of nitrogen or noble gas. The way in which the carbon dioxide is removed is not crucial to the process according to the invention. As mentioned, however, substantially complete removal of carbon dioxide to a residual content of less than 20 ppm is generally not possible by standard distillation under reduced pressure.

Tertiary phosphines or peralkylated phosphorus acid triamides are used as catalysts in the process according to the invention. Mixtures of tert. phosphines and peralkylated phosphorus acid triamides may of course also be used, although this is less preferred. Suitable tert. phosphines include, in particular, aliphatic, araliphatic or mixed aliphaticaromatic tert. phosphines having a molecular weight of 76 to about 500. Examples include compounds corresponding to the formula

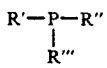

wherein R', R" and R'" may be the same or different and represent $C_1$–$C_{10}$, preferably $C_2$–$C_8$ alkyl groups; $C_7$–$C_{10}$, preferably $C_7$ aralkyl groups; or $C_6$–$C_{10}$, preferably $C_6$ aryl groups, provided that at most one of the substituents is an aryl group and preferably at least one of the substituents is an alkyl group; two of the substituents may form (with the phosphorus atom) a 4- to 6-membered ring containing phosphorus as hetero atom, in which case the third substituent is a $C_1$–$C_4$ alkyl group.

Examples of suitable tert.-phosphines are triethyl phosphine, dibutyl ethyl phosphine, tri-n-propyl phosphine, triisopropyl phosphine, tri-tert.-butyl phosphine, tribenzyl phosphine, benzyl dimethyl phosphine, dimethyl phenyl phosphine, tri-n-butyl phosphine, triisobutyl phosphine, triamyl phosphine, trioctyl phosphine or butyl phosphacyclopentane. Tri-(n-butyl)-phosphine is a particularly suitable catalyst for the process according to the invention.

Peralkylated phosphorus acid triamides suitable for use as catalysts include organic compounds corresponding to the formula

wherein the individual substituents R may be the same or different, preferably the same, and represent $C_1$–$C_{10}$, preferably $C_1$–$C_4$ alkyl radicals; $C_7$–$C_{10}$, preferably $C_7$ aralkyl radicals; or $C_6$–$C_{10}$, preferably $C_6$ cycloalkyl radicals. It can be seen from this definition of the substituents R that the expression "peralkylated" should be broadly interpreted to include not only alkyl radicals but also cycloalkyl and aralkyl radicals as possible substituents of the nitrogen atom. However, the peralkylated phosphorus acid triamides to be used as catalysts in accordance with the invention are preferably those corresponding to the above general formula in which all the substituents R are $C_1$–$C_4$ alkyl radicals, preferably methyl radicals. Permethylated phosphorus acid triamide, i.e., tris-(dimethylamino)phosphine, is the preferred catalyst from the group of phosphorus acid triamides which may be used in the process according to the invention.

The catalysts mentioned are used in a quantity of about 0.01 to 2% by weight, preferably about 0.1 to 1% by weight and more preferably about 0.1 to 0.5% by weight, based on the total quantity of HDI.

The process according to the invention is preferably carried out in the absence of solvents, although this does not preclude the presence of standard lacquer solvents during the oligomerization reaction. Examples of these solvents include esters such as butyl acetate or ethoxyethyl acetate; ketones such as methyl isobutyl ketone or methyl ethyl ketone; hydrocarbons such as xylene; and mixtures of such solvents. However, since unreacted HDI is removed after the reaction, the presence of such solvents during the reaction causes unnecessary additional expense.

The process according to the invention may be carried out, for example, as described in DE-OS 1,670,720, DE-OS 3,432,081 (U.S. Pat. No. 4,614,785, herein incorporated by reference) or DE-OS 3,437,635. For example, the HDI which is substantially free from carbon dioxide may initially be introduced into a suitable stirred reactor, followed by the addition of the catalyst at about 0° to 100° C., preferably about 20° to 70° C., after which the reaction mixture is kept at a temperature of about 0° to 100° C., preferably about 20° to 70° C. by cooling or heating, preferably with stirring. It is advantageous to pass a stream of dry nitrogen or noble gas, for example argon, through the reaction mixture throughout the reaction. The progress of the reaction may be followed by determination of the NCO content of the reaction mixture. The reaction is generally terminated after reaching a degree of oligomerization of about 5 to 70, preferably 15 to 40%. By "degree of oligomerization" is meant the percentage of isocyanate groups which react to form dimers or trimers. This degree of oligomerization corresponds to an NCO content of the reaction mixture of 15 to 47.5% by weight, preferably 30 to 42.5% by weight.

The reaction is terminated by the addition of a catalyst poison which neutralizes the effect of the catalyst. Suitable catalyst poisons include the alkylating or acylating agents mentioned in DE-OS 1,670,720, sulfur and, in particular, the sulfonyl isocyanates recommended for this purpose in DE-OS 3,432,081 (U.S. Pat. No. 4,614,785, herein incorporated by reference). Trialkyl siloxy sulfonyl isocyanates, such as trimethyl siloxy sulfonyl isocyanate, are also suitable. The catalyst poison is used in an at least a half-molar quantity, based on the catalyst. The molar ratio of catalyst to catalyst poison is preferably 1:0.5 to 1:2.

After termination of the reaction, the free, unreacted HDI present in the reaction mixture is removed by suitable means, for example by extraction (for example using n-hexane as extractant) or preferably by thin-layer distillation in a high vacuum at about 110° to 180° C., preferably (due to the heat sensitive uretdione groups) at 110° to 130° C. to a residual content of at most 0.5% by weight.

The products obtained by the process according to the invention are distinguished from known products by less coloration because less catalyst is required in the process according to the invention. They are generally colorless to faintly yellow-colored liquids having a color value (HAZEN) according to DIN 53,409 of less than 200 and generally less than 100. They have a viscosity at 23° C. of about 50 to 3000 mPa.s. They have an NCO content of about 10 to 24% by weight, preferably 18 to 23% by weight. In accordance with the invention both dimerization and trimerization reactions occur. The products obtained by the process according to the invention are mixtures of diisocyanates containing uretdione groups and polyisocyanates containing isocyanurate groups and, because the two reactions take place simultaneously, small quantities of modified polyisocyanates containing both uretdione groups and isocyanurate groups. The molar ratio of uretdione to isocyanurate groups in the products according to the invention is about 1:9 to 9:1, generally about 1:3 to 3:1. It may be influenced within these limits during the process according to the invention by the choice of catalyst and reaction temperature and may be quantitatively determined, for example, by hot titration with dibutylamine solution or IR spectroscopy. The advantage of the process according to the invention over known processes is that it can be carried out in a short time, for example in less than one working day, under very mild conditions and is also very easy to carry out continuously. A major technical advantage is that a high throughput of product can be rapidly obtained in small apparatus.

Since only small quantities of catalyst are used in the process according to the invention, the quantity of deactivator, i.e. the catalyst poison can also be kept correspondingly small. Therefore, the products obtained by the process according to the invention contain very small quantities of secondary products formed from catalyst and catalyst poison which generally remain dissolved and do not affect the subsequent use of the products. Even when technical HDI is used (i.e., HDI which has not been subjected to standard purification by distillation in the presence of weakly basic compounds, such as metal oxides or sodium hydrogen carbonate, to remove traces of chlorine-containing compounds) the products obtained by the process of the present invention are clear and colorless. By virtue of their low viscosity, the products obtained by the process according to the invention are particularly suitable for the production of solventless or low-solvent polyisocyanate polyaddition products, preferably polyurethane lacquers by a reaction with compounds containing at least two isocyanate-reactive groups, preferably hydroxyl groups.

When the products obtained by the process according to the invention are used in accordance with the invention, they may be blocked by blocking agents for isocyanate groups. Suitable blocking agents include the compounds mentioned by way of example in EP-A-10,589, page 15, lines 14 to 26 (U.S. Pat. No. 4,324,879, herein incorporated by reference).

The products obtained by the process according to the invention may be used for the production of high-quality two-component polyurethane lacquers, preferably in combination with the polyhydroxy polyesters, polyhydroxy polyethers and, more preferably, polyhydroxy polyacrylates known from polyurethane lacquer technology. In addition to these relatively high molecular weight polyhydroxyl compounds, these lacquers may also contain low molecular weight polyols, preferably aliphatic polyols. Combinations of the products obtained by the process according to the invention with polyhydroxypolyacrylates represent particularly valuable two-component binders for high-quality, highly weather-resistant lacquers.

Polyamines, preferably in blocked form as polyketimines or oxazolidines, may also be used as reactants for the products obtained by the process according to the invention.

The quantitative ratios in which the optionally blocked polyisocyanates according to the invention and the reactants mentioned are used in the production of polyurethane lacquers are generally selected so that there are about 0.8 to 3, preferably about 0.9 to 1.8 hydroxyl, amino and/or carboxyl groups for every (optionally blocked) isocyanate group.

It is known that, under certain conditions, the uretdione group may also be considered as a reactive group in the same sense as a blocked NCO group. In stoving lacquers which are hardened at elevated temperature, the uretdione group is included as a blocked NCO group in the quantitative ratio of polyisocyanate and reactant.

The hardening reaction may be accelerated with the catalysts known from isocyanate chemistry. Examples include tertiary amines such as triethylamine, pyridine, methyl pyridine, benzyl dimethyl amine, N,N-dimethylaminocyclohexane, N-methyl piperidine, pentamethyl diethylene triamine, N,N'-endoethylene piperazine or N,N'-dimethyl piperazine; and metal salts such as iron(III) chloride, zinc chloride, zinc-Z-ethyl caproate, tin(II)-2-ethyl caproate, dibutyl tin(IV) dilaurate or molybdenum glycolate.

In blocked form the products obtained by the process according to the invention are used in combination with polyhydroxyl compounds of the type mentioned, particularly for the production of stoving lacquers which may be hardened at temperatures of about 80° to 180° C., depending on the blocking agents used, to form high-quality lacquer coatings.

To produce the ready-to-use lacquers, the optionally blocked polyisocyanate, polyfunctional reactant, optional isocyanate polyaddition catalyst and known additives (such as pigments, dyes, fillers and levelling agents) are thoroughly mixed with one another and homogenized in a standard mixing unit, for example in a sand mill, either with or without solvent.

The paints and coating compositions may be applied to the article to be coated in solution, from the melt or in solid form by standard methods such as spread coating, roll coating, casting or spraying.

The lacquers containing the polyisocyanates according to the invention provide films which adhere surprisingly well to metal substrates and are particularly light-stable, color-stable under heat and highly abrasion-resistant. In addition, they are distinguished by considerable hardness, elasticity, very good resistance to chemicals, high gloss, excellent weather resistance and good pigmentability.

In the following examples, all percentages and all quantities in "ppm" are based on weight.

EXAMPLES

Example 1

In a stirred reactor, 1200 g HDI were degassed in about 10 minutes at about 20° C. by application of a vacuum (50 mbar) and vigorous stirring. The gas space of the reactor was then filled with pure nitrogen. A vigorous stream of pure, dry nitrogen was then passed through the liquid for about 1 hour at around 25° C. Whereas the HDI used had an initial $CO_2$ content of 56 ppm, the $CO_2$ content had fallen to 5 ppm after the treatment mentioned. Nitrogen was passed through the reaction mixture for the remainder of the reaction.

1.5 g (approx. 0.007 mol or 0.125%, based on HDI) of tributyl phosphine was then introduced into the liquid heated to 60° C., followed by stirring at that temperature. The progress of the reaction was followed by determination of the isocyanate content. After 2 hours, the NCO content had fallen to 38.6% (degree of oligomerization approx. 22.8%).

The reaction was then terminated by the addition of 1.4 g (approx. 0.007 mol) of trimethyl siloxy sulfonyl isocyanate. After stirring for 30 minutes, monomeric HDI was distilled off in a short-path evaporator at 120° C./0.01 mbar.

474 g of a monomer-free sump product having the following properties were obtained:

| | |
|---|---|
| Viscosity: | 130 mPa.s/20° C. |
| color value (HAZEN), DIN 53,409 | 90 |
| NCO content | 21.4% |
| free HDI content | 0.2% |
| molar ratio of uretdione to | 3:2 |

-continued isocyanurate groups approximately
(as determined by hot titration
with dibutylamine solution
and by IR spectrum).

Example 2 (COMPARISON EXAMPLE)

1200 g of HDI having the same initial CO₂ content as in Example 1 were used in a corresponding reactor. The reactor space above the liquid phase was filled with dry nitrogen, but CO₂ dissolved in the HDI was not removed by blowing out with nitrogen.

The liquid was then heated to 60° C., followed by the addition of 3 g (0.014 mol or 0.25%, based on HDI) of tributyl phosphine. The reaction was initiated with thorough stirring. After 2 hours, the NCO content had only fallen to 47.3%, after 8 hours to 43.4% and after 13 hours to 40.2%. The reaction was then terminated by the addition of 2.8 g of trimethyl silyloxysulfonyl isocyanate. Further processing was carried out as in Example 1.

402 g of a viscous liquid having the following properties were obtained:

| viscosity | 120 mPa.s/23° C. |
|---|---|
| color value (HAZEN), DIN 53,409 | 170 |
| NCO content | 22.0% |
| free HDI content | 0.2% |

Result of the comparison:

The process according to the invention takes place several times more quickly with less catalyst, less deactivator and a high yield. The end product had a better color value.

When Comparison Example 2 was repeated using the quantity of catalyst from Example 1, the reaction took even longer. After reaching 42.0%, there was very little change in the NCO content.

Example 3

Example 6 of DE-OS 3,432,081 (Example 6 of U.S. Pat. No. 4,614,785) was repeated and modified in accordance with the present invention. 1 g of freshly distilled hexamethyl phosphorous acid triamide was added to 400 g of HDI freed from carbon dioxide as in Example 1 (in Example 6 of DE-OS 3,432,081, 4 g catalyst were added to 400 g HDI). After 45 minutes at 60° C., the NCO content measured 38.8% (comparison 40.0%). Working up (distillation, etc.) provided 190 g of a light yellow colored polyisocyanate (comparison 152 g).

The comparison shows that the process according to the invention gives a better yield with less catalyst.

Examples 4 to 8

These examples illustrate the range of variation of the process according to the invention in regard to the quantity of catalyst and the temperature. Carbon dioxide was removed to a residual content of 2 to 10 ppm by blowing out with nitrogen at 40° to 60° C.

The results are set out in Table 1 which sets forth the quantity of catalyst, the reaction temperature and reaction time and also the NCO content on termination of the reaction. Table 2 shows the properties of the end product.

TABLE 1

| Example | HDI (g) | CO₂ content after blowing out with nitrogen | Tributyl phosphine catalyst | Reaction temperature (°C.) | NCO content on deactivation | Reaction time |
|---|---|---|---|---|---|---|
| 4 | 1600 | 2 ppm | 4 g (0.25%) | 23 | 37.5% | 9 h |
| 5 | 1600 | 7 ppm | 2 g (0.125%) | 35 | 38.8% | 5 h |
| 6 | 1600 | 10 ppm | 2 g (0.125%) | 40 | 41.0% | 1.5 h |
| 7 | 1600 | 2 ppm | 8 g (0.5%) | 50 | 22.1% | 6 h |
| 8 | 1600 | 4 ppm | 1 g (0.06%) | 40 | 40.2% | 10 h |

TABLE 2

| Example | Quantity of product after removal of HDI | NCO content (%) | Viscosity/ 23° C. (mPa.s) | Free HDI content (%) |
|---|---|---|---|---|
| 4 | 698 g | 21.1 | 160 | 0.4 |
| 5 | 625 g | 21.8 | 140 | 0.4 |
| 6 | 550 g | 22.6 | 130 | 0.2 |
| 7 | 1240 g | 15.5 | 15000 | 0.1 |
| 8 | 600 g | 21.8 | 140 | 0.05 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate mixture containing isocyanurate groups and uretdione groups in a molar ratio of about 1:9 to 9:1 which comprises oligomerizing a portion of the isocyanate groups of hexamethylene diisocyanate, which contains less than 20 ppm by weight of carbon dioxide, in the presence of a trialkyl phosphine and/or peralkylated phosphorous acid triamide dimerization and trimerization catalyst to the desired degree of oligomerization, terminating the reaction by the addition of a catalyst poison and removing unreacted hexamethylene diisocyanate to a residual content of at least 0.5% by weight.

2. The process of claim 1 wherein said hexamethylene diisocyanate is freed from carbon dioxide by passing a stream of nitrogen or noble gas through the hexamethylene diisocyanate until the residual carbon dioxide content is less than 20 ppm by weight.

3. The process of claim 1 wherein said catalyst comprises tri-(n-butyl)-phosphine or tris-(dimethylamino)-phosphine.

4. The process of claim 2 wherein said catalyst comprises tri-(n-butyl)-phosphine or tris-(dimethylamino)-phosphine.

5. A polyisocyanate mixture containing isocyanurate groups and uretdione groups in a molar ratio of about 1:9 to 9:1 which is prepared by a process comprising oligomerizing a portion of the isocyanate groups of hexamethylene diisocyanate, which contains less than 20 ppm by weight of carbon dioxide, in the presence of a trialkyl phosphine and/or peralkylated phosphorous acid triamide dimerization and trimerization catalyst to the desired degree of oligomerization, terminating the reaction by the addition of a catalyst poison and removing unreacted hexamethylene diisocyanate to a residual content of at least 0.5% by weight.

6. The polyisocyanate mixture of claim 5 wherein said hexamethylene diisocyanate is freed from carbon dioxide by passing a stream of nitrogen or noble gas through the hexamethylene diisocyanate until the residual carbon dioxide content is less than 20 ppm by weight.

7. The polyisocyanate mixture of claim 5 wherein said catalyst comprises tri-(n-butyl)-phosphine or tris-(dimethylamino)-phosphine.

8. The polyisocyanate mixture of claim 6 wherein said catalyst comprises tri-(n-butyl)-phosphine or tris-(dimethylamino)-phosphine.

9. A process for the production of a polyisocyanate mixture containing isocyanate groups and unretdione groups in a molar ratio of about 1:9 to 9:1 which comprises oligomerizing a portion of the isocyanate groups of hexamethylene diisocyanate, which contains less than 10 ppm by weight of carbon dioxide, in the presence of a trialkyl phosphine and/or peralkylated phosphorous acid triamide dimerization and trimerization catalyst to the desired degree of oligomerization, terminating the reaction by the addition of a catalyst poison and removing unreacted hexamethylene diisocyanate to a residual content of at least 0.5% by weight.

10. The process of claim 9 wherein said hexamethylene diisocyanate is freed from carbon dioxide by passing a stream of nitrogen or noble gas through the hexamethylene diisocyanate until the residual carbon dioxide content is less than 10 ppm by weight.

11. The process of claim 9 wherein said catalyst comprises tri-(n-butyl)-phosphine or tris-(dimethylamino)-phosphine.

12. The process of claim 10 wherein said catalyst comprises tri-(n-butyl)-phosphine or tris-(dimethylamino)-phosphine.

13. A polyisocyanate mixture containing isocyanate groups and uretdione groups in a molar ratio of about 1:9 to 9:1 which is prepared by a process comprising oligomerizing a portion of the isocyanate groups of hexamethylene diisocyanate, which contains less than 10 ppm by weight of carbon dioxide, in the presence of a trialkyl phosphine and/or prealkylated phosphorous acid triamide dimerization and trimerization catalyst to the desired degree of oligomerization, terminating the reaction by the addition of a catalyst poison and removing unreacted hexamethylene diisocyanate to a residual content of at least 0.5% by weight.

14. The polyisocyanate mixture of claim 13 wherein said hexamethylene diisocyanate is freed from carbon dioxide by passing a stream of nitrogen or noble gas through the hexamethylene diisocyanate until the residual carbon dioxide content is less than 10 ppm by weight.

15. The polyisocyanate mixture of claim 13 wherein said catalyst comprises tri-(n-butyl)-phosphine or tris-(dimethylamino)-phosphine.

16. The polyisocyanate mixture of claim 14 wherein said catalyst comprises tri-(n-butyl)-phosphine or tris-(dimethylamino)-phosphine.

* * * * *